United States Patent
Iio et al.

(10) Patent No.: US 8,372,104 B2
(45) Date of Patent: Feb. 12, 2013

(54) LANCET FOR BLOOD COLLECTION AND PUNCTURE NEEDLE UNIT

(75) Inventors: Toshiaki Iio, Saijyo (JP); Yoshinori Amano, Saijyo (JP); Koya Kurokawa, Saijyo (JP); Noriyuki Shinohara, Niihama (JP)

(73) Assignee: Panasonic Corporation, Osaka (JP)

( * ) Notice: Subject to any disclaimer, the term of this patent is extended or adjusted under 35 U.S.C. 154(b) by 382 days.

(21) Appl. No.: 12/644,445

(22) Filed: Dec. 22, 2009

(65) Prior Publication Data
US 2010/0100113 A1 Apr. 22, 2010

Related U.S. Application Data

(62) Division of application No. 11/011,184, filed on Dec. 15, 2004, now Pat. No. 7,763,042.

(30) Foreign Application Priority Data

Dec. 16, 2003 (JP) ................................. 2003-418527
Jan. 5, 2004 (JP) ................................. 2004-000615

(51) Int. Cl.
*A61B 17/14* (2006.01)
(52) U.S. Cl. ...................................... 606/181
(58) Field of Classification Search .................. 606/181, 606/182; 600/573, 583
See application file for complete search history.

(56) References Cited

U.S. PATENT DOCUMENTS

| 4,924,879 | A | 5/1990 | O'Brien |
| 6,210,421 | B1 | 4/2001 | Bocker et al. |
| 6,409,740 | B1 | 6/2002 | Kuhr et al. |
| 7,604,118 | B2 * | 10/2009 | Iio et al. ............... 206/365 |
| 7,763,042 | B2 * | 7/2010 | Iio et al. ............... 606/182 |

FOREIGN PATENT DOCUMENTS

| JP | 6-038909 | 5/1994 |
| JP | 2000-237172 | 9/2000 |
| JP | 2000-143131 | 5/2002 |

OTHER PUBLICATIONS

Official Action dated Jan. 12, 2010 issued in corresponding Japanese Patent Application No. 2004-000615 with English translation.

* cited by examiner

*Primary Examiner* — Tuan V Nguyen
(74) *Attorney, Agent, or Firm* — Wenderoth, Lind & Ponack, L.L.P.

(57) ABSTRACT

A lancet having a slider with a puncture needle holding mechanism at one end thereof, and having a cam ring with a continuous cam groove, rotatable about a support shaft, and with a cam ring claw and an anti-return claw restricting the rotation. The lancet also having a ring spring applying a force to rotate the cam ring, having a rotatable stopper arm holding and releasing the rotation of the cam ring, and having a rotatable ratchet restricting the direction of rotation of the cam ring. A puncture needle unit including a puncture needle body integrally molded with a protrusion fitted to the lancet, a rotation stop rib, a puncture needle, and a puncture needle cap lightly pressed into the puncture needle body.

14 Claims, 14 Drawing Sheets

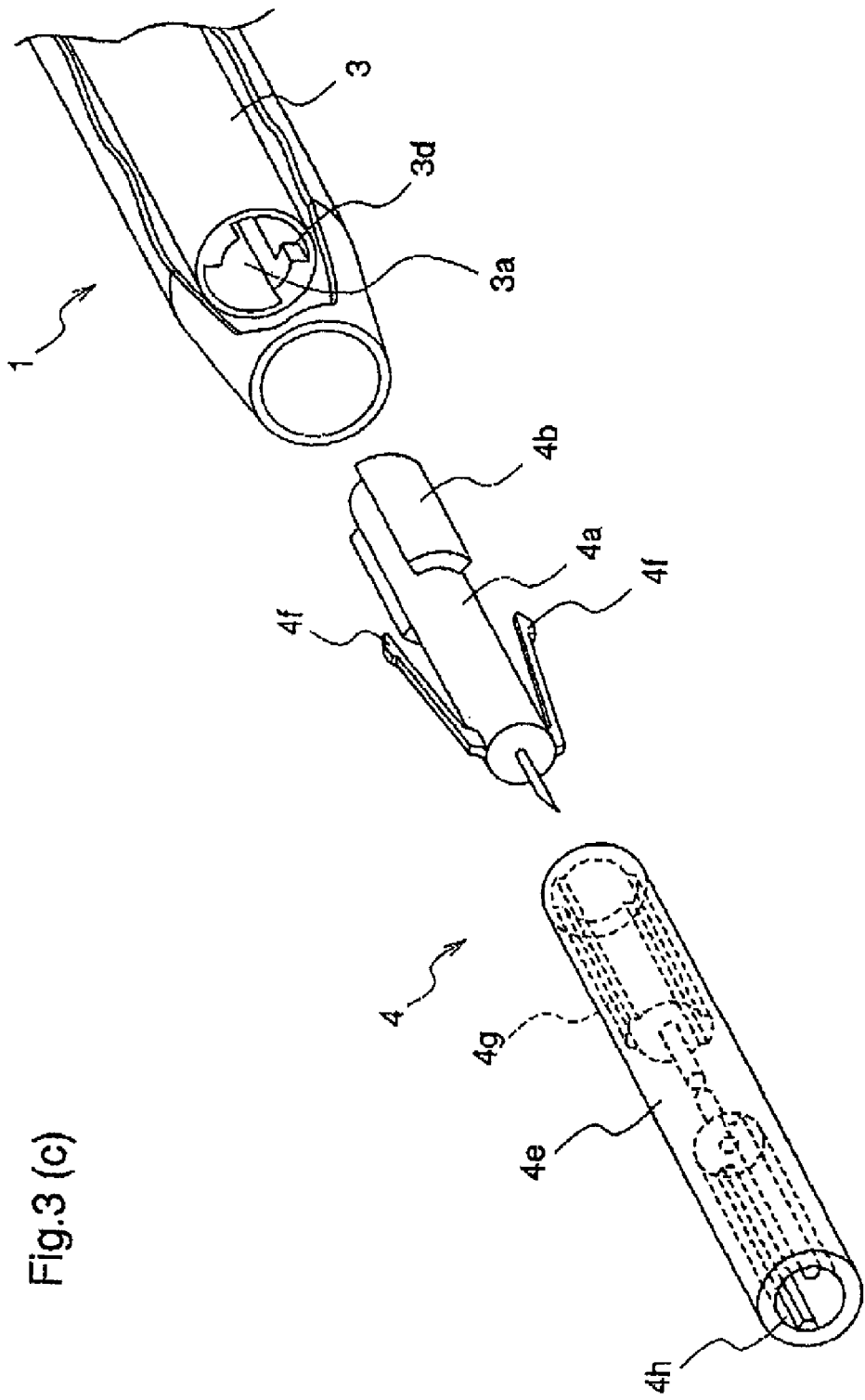

US 8,372,104 B2

LANCET FOR BLOOD COLLECTION AND PUNCTURE NEEDLE UNIT

The present application is a divisional of U.S. application Ser. No. 11/011,184, filed Dec. 15, 2004, which is now U.S. Pat. No. 7,763,042.

FIELD OF THE INVENTION

The present invention relates to a lancet for blood collection and a puncture needle unit, which are used for measuring blood sugar or the like. More specifically, the invention relates to a technique for performing puncture using the lancet, and a technique for attaching/detaching the puncture needle unit to/from the lancet.

BACKGROUND OF THE INVENTION

A conventional lancet will be described with reference to FIG. 13. A disposal puncture needle 127 is attached to a lancet 120, and a fingertip or arm of a patient is punctured with a needle 127A provided at the front end of the puncture needle 127 to collect blood from the punctured portion. The typical lancet 120 comprises a cylindrical body 121, and a cap 126. A slidable puncture rod 123 for holding the puncture needle 127 is incorporated in the body 121, and the puncture rod 123 has a first spring 122 for projecting the attached puncture needle 127, a second spring 124 for backing off the projected puncture needle 127, and a launch button 125 for releasing the compressed first spring 122.

The lancet 120 is used as follows. Initially, the cap 126 is removed from the body 121, and the puncture needle 127, from which a protection cap 127B is twisted and removed, is attached to the puncture rod 123 incorporated in the body, and the cap 126 is again put on the body. Then, the first spring 122 is compressed to set the lancet 120 in a state where puncture is possible (puncture-ready state), and a puncture target pressing surface 126A of the cap 126 is applied to a target to be punctured, such as a fingertip. When the launch button 125 is pressed, the puncture rod 123 slides, and simultaneously, the puncture needle 127 attached to a holder 123A also slides, and the puncture needle 127 hits the inner wall of the cap 126. At this time, the tip of the needle 127A slightly protrudes from a puncture hole 126B, and punctures the fingertip or the like. Thereafter, the puncture needle 127 is immediately removed from the fingertip or the like by the second spring 124. Thereby, the lancet 122 collects blood. (Refer to Japanese Published Patent Application No. 2000-237172 (Pages 3 and 4, FIG. 1).)

In the conventional lancet, however, in order to execute the puncture operation, initially the puncture needle housed in the blood collection device (lancet) is once held at a position where the first spring is charged and then released, whereby the puncture needle is displaced in the puncture direction, i.e., it moves toward a body region to be punctured. After the puncture needle hits the lancet body, the puncture needle is backed off to the initial position by the function of the second spring, and stopped. According to this method, shock, sound, and vibration during puncture are considerable. Further, since the puncture needle vibrates due to the balance of the spring forces, the puncture needle might puncture the same portion or its vicinity a few times. Further, when attaching or detaching the puncture needle to/from the lancet, the needle is unprotected because it is not covered with the protection cap, and the puncture rod easily moves because it is held by only the spring, leading to puncture by mistake.

SUMMARY OF THE INVENTION

The present invention is made to solve the above-mentioned problems and has for its object to provide a lancet for blood collection and a puncture needle unit, which are able to reduce pain and fear of a patient due to shock, sound, and vibration when performing puncture using a puncture needle, and prevent the puncture needle from puncturing the same portion a few times, and further, ensure excellent usability and handling ability with safety.

Other objects and advantages of the invention will become apparent from the detailed description that follows. The detailed description and specific embodiments described are provided only for illustration since various additions and modifications within the scope of the invention will be apparent to those of skill in the art from the detailed description.

According to a first aspect of the present invention, there is provided a lancet for puncturing a human body with a puncture needle to collect bodily fluids from the human body, comprising: a slider which is able to hold a puncture needle at one end, and is reversibly slidable in a linear direction so that a puncture operation by the puncture needle is carried out; a cam ring which is flat-shaped and rotatable about its axis, has a cam groove that is engaged with a cam follower provided on the slider within its rotation plane, and slides the slider by its rotation operation; an elastic force application member for applying a rotation force in a predetermined direction to the cam ring to slide the slider in a puncture direction; a stopper arm for stopping the rotation of the cam ring to which a force is applied by the elastic force application member, or releasing the stopping; and an anti-reverse-rotation mechanism which is implemented by a ratchet mechanism for preventing reverse rotation of the cam ring after the puncture operation. Therefore, it is possible to provide a lancet for blood collection which reduces shock, sound, and vibration during puncture, prevents plural times of puncture by a puncture needle, gives less pain and fear to a patient, and is highly operable and safely handleable.

According to a second aspect of the present invention, in the lancet according to the first aspect, the anti-reverse-rotation mechanism releases the stopping of rotation of the cam ring to which a force is applied by the elastic force application member, by the releasing operation of the stopper arm; and when the slider moves with the rotation of the cam ring and thereby a puncture operation is carried out and then the slider moves in a direction that goes apart from the puncture direction with further rotation of the cam ring, the anti-reverse-rotation mechanism restricts the rotation of the cam ring in one direction so as to prevent the slider from moving in the puncture direction again. Therefore, it is possible to restrict rotation of the cam ring in one direction.

According to a third aspect of the present invention, in the lancet according to the first aspect, the stopper arm has a stopper claw that contacts a cam ring claw of the cam ring, in a puncture-ready position where the puncture needle is backed off into the lancet, and a rotation force applied to the cam ring by the elastic force application member is active; when the stopper arm is pressed and rotated in the above-mentioned state, the contact of the stopper claw of the stopper arm and the cam ring claw is released, whereby the cam ring rotates in a predetermined position; and when the slider slides in the puncture direction by the rotation of the cam ring and thereby the cam ring rotates exceeding a maximum protrusion position of the puncture needle, an anti-reverse claw of the cam ring passes over a ratchet claw of the ratchet mechanism while bending the ratchet mechanism, and catches the ratchet claw to prevent the cam ring from rotating in the opposite direction. Therefore, it is possible to provide a lancet for blood collection which prevents plural times of puncture by a puncture needle, gives less pain and fear to a patient, and is highly operable and safely handleable.

According to a fourth aspect of the present invention, in the lancet according to the first aspect, the stopper arm has a stopper for restricting the amount of rotation of the stopper arm toward the cam ring; and the ratchet has a stopper for restricting the amount of rotation of the ratchet toward the cam ring. Therefore, reliabilities of operations of the stopper arm and the ratchet are respectively increased, and an excessive load on the cam ring due to friction is eliminated.

According to a fifth aspect of the present invention, the lancet as defined in the first aspect of the present invention further comprising: a set ring which is rotatably provided on the same axis as the cam ring; and a force transfer mechanism for transferring a rotation force of the set ring only in one direction; wherein the rotation force of the set ring is transferred to the cam ring through the force transferring mechanism. Therefore, the slider is reliably held when setting or removing a puncture needle. In addition, operability and reliability for setting a puncture needle in a puncture-ready state are increased.

According to a sixth aspect of the present invention, in the lancet according to the first aspect, the elastic force application member is implemented by a ring spring. Therefore, it is possible to efficiently apply a force to the cam ring with a simple construction.

According to a seventh aspect of the present invention, there is provided a lancet for puncturing a human body with a puncture needle to collect bodily fluids from the human body, comprising: a slider which is able to hold a puncture needle at one end, and is reversibly slidable in a linear direction so that a puncture operation by the puncture needle is carried out; a link mechanism which is coupled to the other end of the slider; a flywheel which is mounted rotatably with respect to the link mechanism, and is coupled to the link mechanism by implanting a rotation knot shaft as a shaft on the other end of the link mechanism coupled to the slider, in the flywheel; an elastic force application member for applying a rotation force in a predetermined direction to the flywheel to slide the slider in a puncture direction through the link mechanism; a stopper arm for stopping the rotation of the flywheel to which a force is applied by the elastic force application member, or releasing the stopping; a set lever mechanism which is engaged with a wheel set pin provided on the flywheel, and rotates the flywheel only in one direction, thereby setting the slider in a puncture-ready position; and an anti-reverse-rotation mechanism which prevents reverse rotation of the flywheel after the puncture operation. Therefore, it is possible to provide a lancet for blood collection which reduces shock, sound, and vibration during puncture, prevents plural times of puncture by a puncture needle, gives less pain and fear to a patient, and is highly operable and safely handleable.

According to an eighth aspect of the present invention, in the lancet according to the seventh aspect, the anti-reverse-rotation mechanism releases the stopping of rotation of the flywheel to which a force is applied by the elastic force application member, by the releasing operation of the stopper arm; and when the slider moves with the rotation of the flywheel and thereby a puncture operation is carried out and then the slider moves in a direction that goes apart from the puncture direction with further rotation of the flywheel, the anti-reverse-rotation mechanism restricts the rotation of the flywheel in one direction so as to prevent the slider from moving in the puncture direction again. Therefore, it is possible to prevent reverse rotation of the flywheel.

According to a ninth aspect of the present invention, in the lancet according to the seventh aspect, the stopper arm has a stopper claw that contacts the rotation knot shaft implanted in the flywheel, in a puncture-ready position where the puncture needle is backed off into the lancet, and a rotation force applied to the flywheel by the elastic force application member is active; when the stopper arm is pressed and rotated in the above-mentioned state, the contact of the stopper claw of the stopper arm and the rotation knot shaft is released, whereby the flywheel rotates in a predetermined position; and when the slider slides in the puncture direction by the rotation of the flywheel through the link mechanism and thereby the flywheel rotates exceeding a maximum protrusion position of the puncture needle, the rotation knot shaft passes over an anti-reverse-rotation claw of the anti-reverse-rotation mechanism while bending the anti-reverse-rotation mechanism, and catches the anti-reverse-rotation claw to prevent the flywheel from rotating in the opposite direction. Therefore, it is possible to provide a lancet for blood collection which reduces shock, sound, and vibration during puncture, prevents plural times of puncture by a puncture needle, gives less pain and fear to a patient, and is highly operable and safely handleable.

According to a tenth aspect of the present invention, in the lancet according to the seventh aspect, the set lever mechanism is provided with an elastic member for returning the set lever mechanism back to the initial state when the contact of the front end of the stopper arm with the rotation knot shaft is released. Therefore, it is possible to reduce the rotation load of the flywheel during the puncture operation.

According to an eleventh aspect of the present invention, in the lancet according to the seventh aspect, the rotation knot shaft is constituted as a catch mechanism for puncture preparation in which the slider is fixed to a start position of one reciprocating operation of the slider in its axis direction, by being engaged with the front end of the stopper arm. Therefore, it is possible to efficiently stop the rotation of the flywheel.

According to a twelfth aspect of the present invention, in the lancet according to the eleventh aspect, the elastic force application member applies a force to the rotation knot shaft so as to rotate the flywheel around its axis in a predetermined rotation direction. Therefore, it is possible to efficiently apply a force to the flywheel with a simple construction.

According to a thirteenth aspect of the present invention, in the lancet according to the eleventh aspect, the elastic force application member for applying a force to the rotation knot shaft is implemented by a kick spring. Therefore, it is possible to reliably obtain a driving force for linearly sending a puncture needle to a puncture position, with a simple construction.

According to a fourteenth aspect of the present invention, in the lancet according to the eleventh aspect, in the puncture-ready state, the center of the rotation knot shaft is located on the slider side with respect to the rotation center of the flywheel. Therefore, it is possible to carry out puncture after the flywheel is stopped completely.

According to a fifteenth aspect of the present invention, in the lancet according to any of the first to fourteenth aspects, wherein the puncture needle has a safety claw which is engaged with the inner surface of an external case of the lancet to prevent the puncture needle from dropping when the puncture needle is detached from the lancet. Therefore, it is possible to provide a lancet for blood collection which can be handled more safely.

According to a sixteenth aspect of the present invention, in the lancet according to the first or seventh aspect, the slider has a fitting and fixing hole for fixing the puncture needle; and the puncture needle is a puncture needle unit comprising a puncture needle body and a puncture needle cap, and the puncture needle body has a puncture needle main part having a needle at its front end, a protrusion to be fitted and fixed to the fitting and fixing hole, at an external surface of a base portion of the puncture needle main part, and a rotation stop rib for the puncture needle cap that covers the puncture needle body, at a side surface of an upper portion of the puncture needle body; and the puncture needle cap is fitted to the rotation stop rib and is lightly pressed into the puncture needle body to cover the puncture needle body. Therefore, it is possible to provide a lancet for blood collection and a puncture needle unit, which reduce shock, sound, and vibration during puncture, prevent plural times of puncture by a puncture needle, give less pain and fear to a patient, and are highly operable and safely handleable.

According to a seventeenth aspect of the present invention, in the lancet according to the sixteenth aspect, in the puncture needle unit, the puncture needle main part is snugly fitted and attached to the lancet with the puncture needle cap being attached to the puncture needle body part; and after the puncture needle main part is attached to the lancet, the puncture needle cap is removed from the puncture needle main part. Therefore, it is possible to provide a lancet and a puncture needle unit which are able to safely set a puncture needle.

According to an eighteenth aspect of the present invention, in the lancet according to the sixteenth aspect, the puncture needle unit detaches the puncture needle main part from the lancet as follows: the puncture needle cap is pressed in and snugly fitted to the puncture needle main part after performing the puncture operation; and the puncture needle main part is removed together with the puncture needle cap from the lancet body together. Therefore, it is possible to provide a lancet and a puncture needle unit which are able to safely discard a used puncture needle.

According to a nineteenth aspect of the present invention, in the lancet according to the sixteenth aspect, the puncture needle cap is cylindrical in shape, and has protection slots for protecting the puncture needle after performing the puncture operation from the lancet body, which slots are formed from both of an end and the other end of the cylindrical shape. Therefore, it is possible to safely discard a used puncture needle.

According to a twentieth aspect of the present invention, in the lancet according to the sixteenth aspect, the puncture needle cap is cylindrical in shape, and has a protection slot for protecting the puncture needle, which is formed from an end of the cylindrical shape, and a disposal slot for taking the puncture needle after performing the puncture operation from the lancet body and discarding the needle, which is formed from the other end of the cylindrical shape, and fitting of the puncture needle to the disposal slot is easier than fitting of the puncture needle to the protection slot. Therefore, it is possible to easily and safely discard a used puncture needle.

According to a twenty-first aspect of the present invention, in the lancet according to the twentieth aspect, the disposal slot of the puncture needle cap has an opening that is larger than an opening of the protection slot. Therefore, it is possible to easily and safely discard a used puncture needle.

According to a twenty-second aspect of the present invention, in the lancet according to the sixteenth aspect, the puncture needle body has a safety claw which is engaged with the inner surface of an external case of the lancet to prevent the puncture needle from dropping when the puncture needle body is detached from the lancet; and the puncture needle cap is lightly pressed into the puncture needle body while being fitted to the safety claw, to cover the puncture needle body.

Therefore, it is possible to provide a lancet for blood collection which can be handled more safely.

According to a twenty-third aspect of the present invention, there is provided a puncture needle unit comprising: a puncture needle body, and a puncture needle cap, the puncture needle body having a puncture needle main part having a needle at its front end, a protrusion to be fitted and fixed to a fitting and fixing hole provided on the lancet body, which protrusion is provided on an external surface of a base portion of the puncture needle main part, and a rotation stop rib for the puncture needle cap that covers the puncture needle body, which rib is provided on a side surface of an upper portion of the puncture needle body; and the puncture needle cap being fitted to the rotation stop rib and lightly pressed into the puncture needle body to cover the puncture needle body. Therefore, it is possible to provide a puncture needle unit which reduces shock, sound, and vibration during puncture, prevents plural times of puncture by a puncture needle, gives less pain and fear to a patient, and is highly operable and safely handleable.

According to a twenty-fourth aspect of the present invention, in the puncture needle unit according to the twenty-third aspect, the puncture needle body has a safety claw that is engaged with the inner surface of an external case of the lancet to prevent the puncture needle from dropping when the puncture needle is detached from the lancet; and the puncture needle cap is lightly pressed into the puncture needle body while being fitted to the safety claw, to cover the puncture needle body. Therefore, it is possible to provide a puncture needle unit which can be handled more safely.

BRIEF DESCRIPTION OF THE DRAWINGS

FIG. 3(c) is a perspective view of the puncture needle unit according to the first embodiment, wherein the lancet, the puncture needle body, and the puncture needle cap are separated.

DETAILED DESCRIPTION OF THE PREFERRED EMBODIMENTS

Hereinafter, lancets according to embodiments of the present invention will be described with reference to the drawings.

[Embodiment 1]

Figure 1:
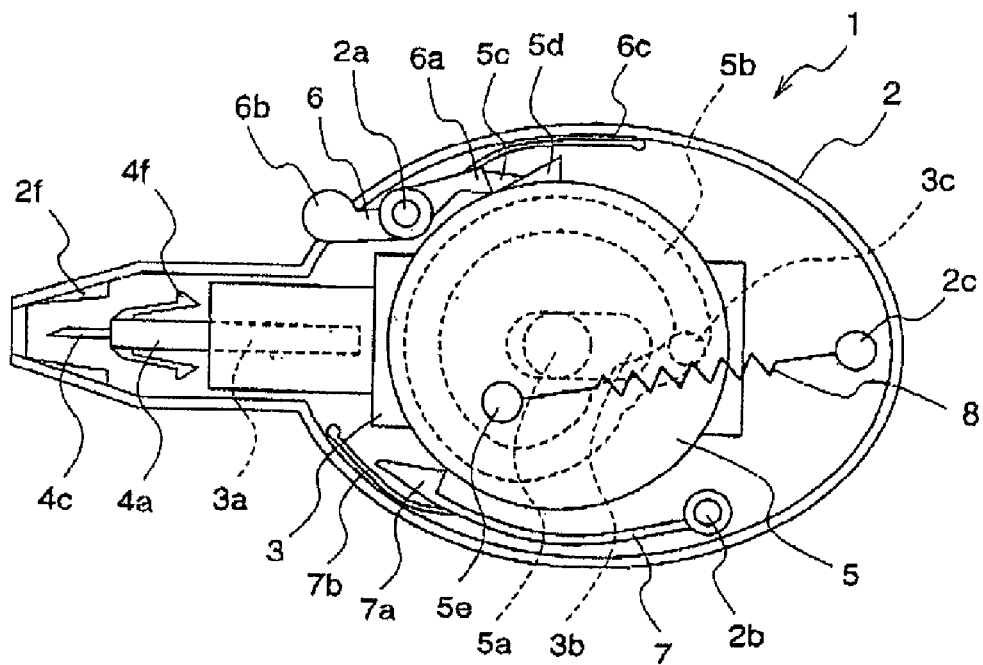
FIG. 1 is a plane view of a lancet according to a first embodiment of the present invention, illustrating a state where puncture is ready.

FIG. 1 is a plane view illustrating a lancet in a puncture-ready state, according to a first embodiment of the present invention.

In FIG. 1, a lancet body 1 according to the first embodiment has a bottom case 2 as a base, and various kinds of parts are incorporated in the bottom case 2. A slider 3 has a puncture needle fixing hole 3a in which a puncture needle body 4a is inserted, a slide groove 3b that guides the slider 3, and a cam follower 3c to be guided by a cam groove 5b, and the slider 3 is reversibly slidable in the longitudinal direction.

The puncture needle body 4a has, at an end thereof, a needle 4c that is able to puncture a fingertip or the like, and an elastic safety claw 4f. The puncture needle body 4a is inserted in the puncture needle fixing hole 3a of the slider 3.

A cam ring 5 is flat in shape, and rotatable about a cam ring support shaft 5a. The cam ring 5 has the continuous cam groove 5b within its rotation plane, and the cam groove 5b guides the cam follower 3c. The cam ring 5 slides the slider 3 by its own rotation. A cam ring claw 5c is provided at the outer circumference of the cam ring 5, and temporarily holds rotation of the cam ring 5 in combination with a stopper arm 6 described later. An anti-return claw 5d provided at the outer circumference of the cam ring 5 has a height different from that of the cam ring claw 5c, and restricts the rotation direction of the cam ring 5 in combination with a ratchet 7 for preventing reverse rotation of the cam ring 5. A cam ring pin 5e has a groove, and is press-fitted into the cam ring 5.

A stopper arm 6 is rotatable about a stopper arm support shaft 2a that is integrally molded with the bottom case 2. The stopper arm 6 has a stopper claw 6a for fixing the cam ring claw 5c at an end, and a stopper arm button 6b at the other end, and stops the rotation of the cam ring 5 or releases the stopping with operation of the stopper arm button 6b. Further, the stopper claw 6a and the anti-return claw 5d have different heights, and therefore, these claws are never engaged with each other. A stopper arm spring 6c is a plastic spring that is integrally molded with the stopper arm 6, and lightly applies a force to the stopper arm 6 clockwise.

Figure 2:
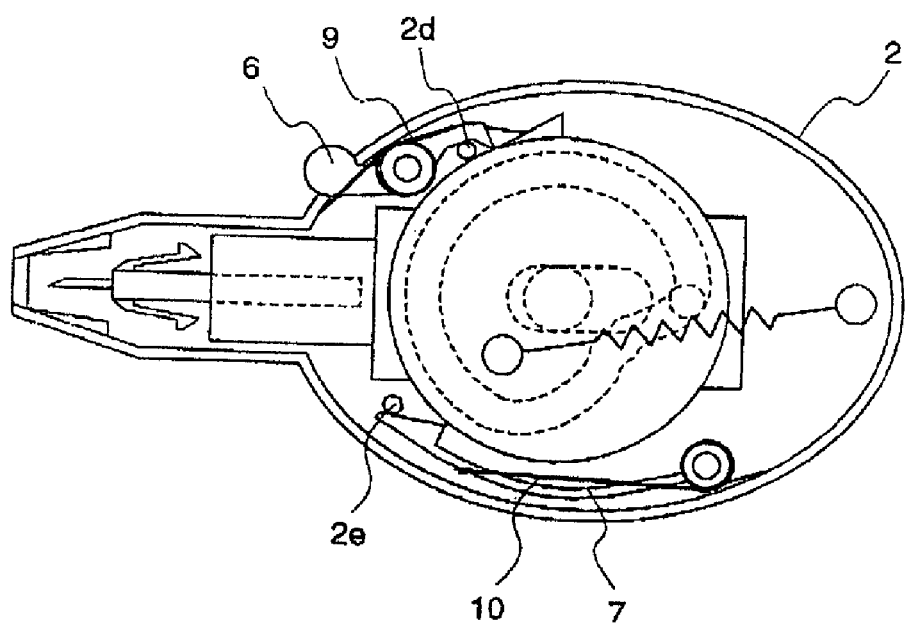
FIG. 2 is a plane view of the lancet according to a first embodiment, illustrating a state where puncture is ready, wherein some of main parts are changed.

While in this first embodiment a plastic spring is used as the stopper arm spring 6c, the stopper arm spring is not restricted thereto. Any spring may be used so long as it can restrict the rotation of the stopper arm. For example, as shown in FIG. 2, instead of the stopper arm spring 6c, a stopper arm spring 9 that is a metal spring may be hanged between the bottom case 2 and the stopper arm 6 to lightly apply a clockwise force to the stopper arm 6. Further, the stopper arm pin 2d may be integrally molded with the bottom case 2, and the stopper arm pin 2d may serve as a stopper for restricting the amount of clockwise rotation of the stopper arm 6. Thereby, reliability of the operation of the stopper arm 6 is improved, and excessive load on the cam ring 5 due to friction is eliminated.

The ratchet 7 is rotatable about a ratchet support shaft 2b that is integrally molded with the bottom case 2, and has, at an end thereof, a ratchet claw 7a that engages with the anti-return claw 5d of the cam ring 5. The ratchet 7 releases stopping of rotation of the cam ring 5 by the releasing operation of the stopper arm 6. After the slider 3 moves with the rotation of the cam ring 5 and thereby puncture is carried out, when the slider 3 moves away from the puncture needle by the further rotation of the cam ring 5, the ratchet 7 restricts the rotation of the cam ring 5 in one direction so as to prevent the slider 3 from again moving in the puncture direction. The ratchet claw 7a is of a height different from that of the cam ring claw 5c and, therefore, these claws are never engaged with each other. A ratchet spring 7b is a plastic spring that is integrally molded with the ratchet 7, and lightly applies a force to the ratchet 7 clockwise.

While in this first embodiment a plastic spring is used as the ratchet spring 7b, the ratchet spring is not restricted thereto. Any spring may be used so long as it can lightly apply a force to the cam ring. For example, as shown in FIG. 2, instead of the ratchet spring 7b, a ratchet spring 10 that is a metal spring may be hanged between the bottom case 2 and the ratchet 7 to lightly apply a clockwise force to the ratchet 7. Further, a ratchet pin 2e may be integrally molded with the bottom case 2, and the ratchet pin 2e may serve as a stopper for restricting the amount of clockwise rotation of the ratchet 7. Thereby, reliability of the operation of the ratchet 7 is improved, and excessive load on the cam ring 5 due to friction is eliminated, whereby the operation of the lancet body becomes smoother.

A ring spring 8 is dangled between a ring spring shaft 2c and the cam ring pin 5e, and applies a force counterclockwise to the cam ring 5 in the state shown in FIG. 1 to slide the slider 3 in the puncture direction.

A puncture needle stopper 2f hitches on the safety claw 4f even when the puncture needle body 4a is detached from the slider 3.

Next, a puncture needle unit to be used for the lancet 1 according to the first embodiment will be described.

Figure 3A:
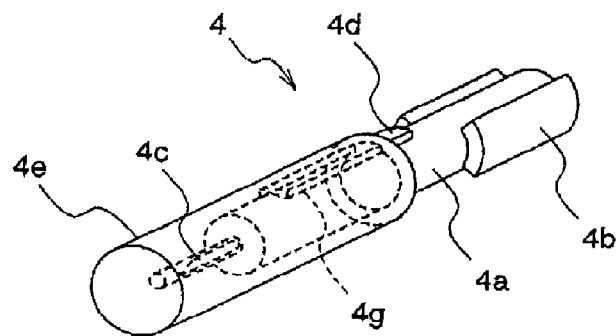
FIG. 3(a) is a perspective view of a puncture needle unit according to the first embodiment, wherein a puncture needle body and a puncture needle cap are united.
Figure 3B:
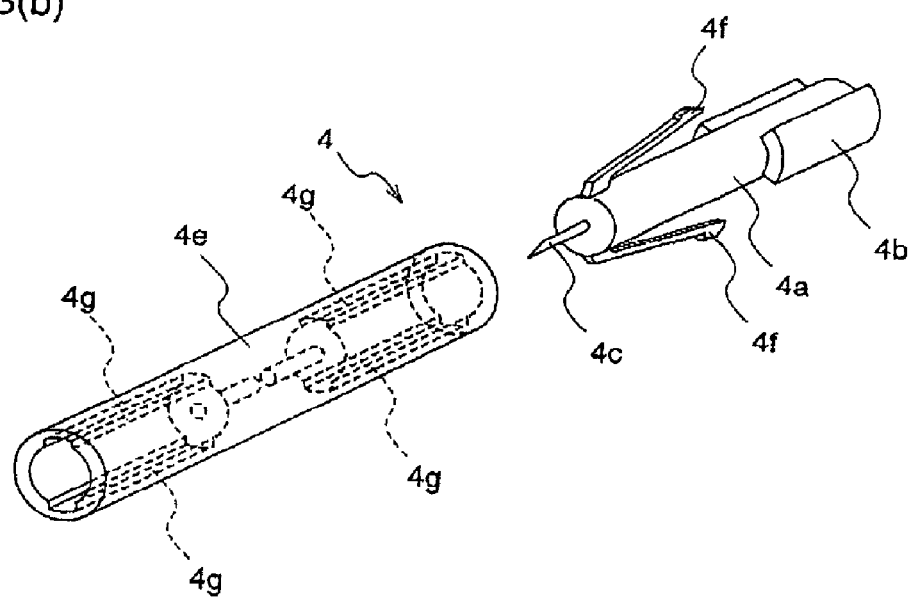
FIG. 3(b) is a perspective view of the puncture needle unit according to the first embodiment, wherein the puncture needle body and the puncture needle cap are separated.

FIGS. 3(a) to 3(c) are diagrams illustrating a puncture needle unit according to the first embodiment of the present invention, and the puncture needle unit has, at an end thereof, a puncture needle body, and a cap that covers the puncture needle body. To be specific, FIG. 3(a) is a perspective view illustrating the puncture needle body and the cap which are united to each other, FIG. 3(b) is a perspective view illustrating the puncture needle body and the cap which are separated from each other, and FIG. 3(c) is a perspective view illustrating the lancet, the puncture needle body, and the cap which are separated from each other.

Reference numeral 4 denotes the puncture needle unit in which the cap 4e is lightly press-fitted to the puncture needle body 4a. The puncture needle body 4a has a protrusion 4 at an outer surface of a base part thereof, a rotation stop rib 4d at a side surface of an upper part thereof, and a needle 4c at an end. The puncture needle cap 4e can be snugly fitted to the puncture needle body 4a, and a slot 4g that protects the puncture needle is formed in accordance with the rotation stop rib 4d. Safety claws 4f are implemented by, for example, plastic springs that are elastic and integrally molded with the puncture needle body 4a. When the cap 4e is pulled out, the safety claws 4f expand outward. The safety claws also function as rotation stop ribs 4d.

Like the puncture needle cap 4e shown in FIG. 3(b), two slots 4g of the same shape may be formed from the both ends of the cap. Alternately, like the cap 4e shown in FIG. 3(c), two slots of different shapes may be formed, i.e., a slot 4g of the same shape as that shown in FIG. 3(b) is formed at an end of the cap while a disposal slot 4h of a different shape is formed at the other end of the cap. The use of the puncture cap 4e facilitates handling of the puncture needle body 4a when discarding the puncture needle body. That is, the slot 4h of the puncture needle cap 4e has a larger release opening so as to facilitate insertion of the rotation stop rib 4d or the safety claw 4f, when the puncture needle body 4a is pulled out of the puncture needle fixing hole 3a formed in the slider 3 after puncture has been completed.

Further, at an end of the slider 3, a puncture needle fixing hole 3a as shown in FIG. 3(c) is provided, in which a catch claw 3d for catching the protrusion 4b is formed.

Figure 4A:
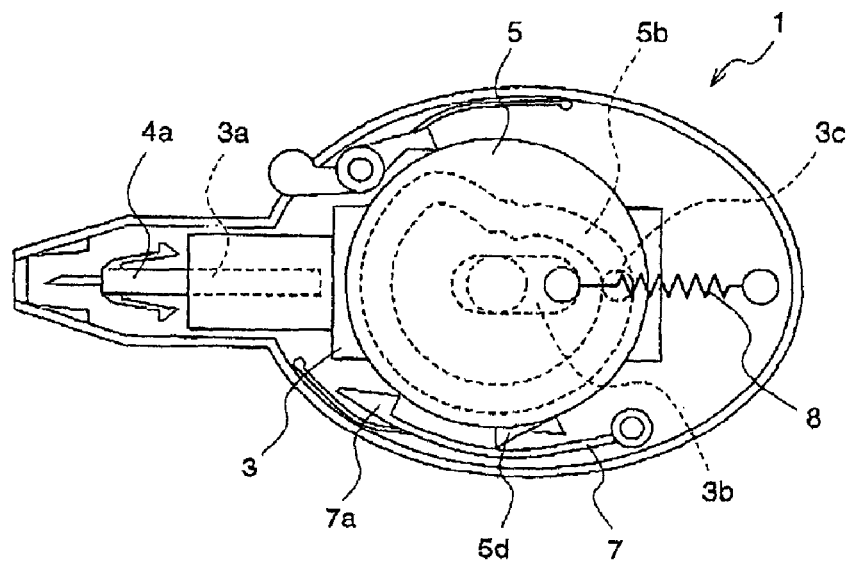
FIG. 4(a) is a plane view illustrating a puncture operation of the lancet according to the first embodiment, illustrating a puncture needle set position.
Figure 4B:
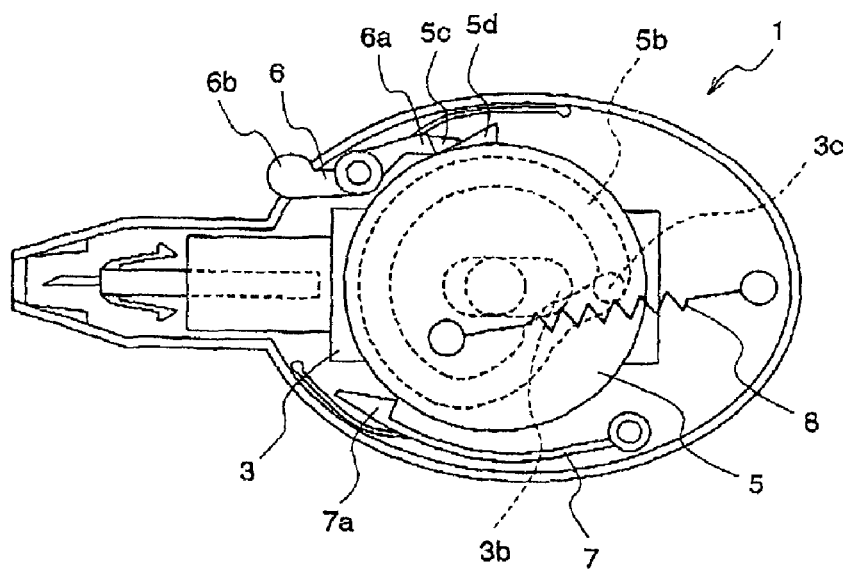
FIG. 4(b) is a plane view illustrating the puncture operation of the lancet according to the first embodiment, illustrating a puncture operation ready position.
Figure 4C:
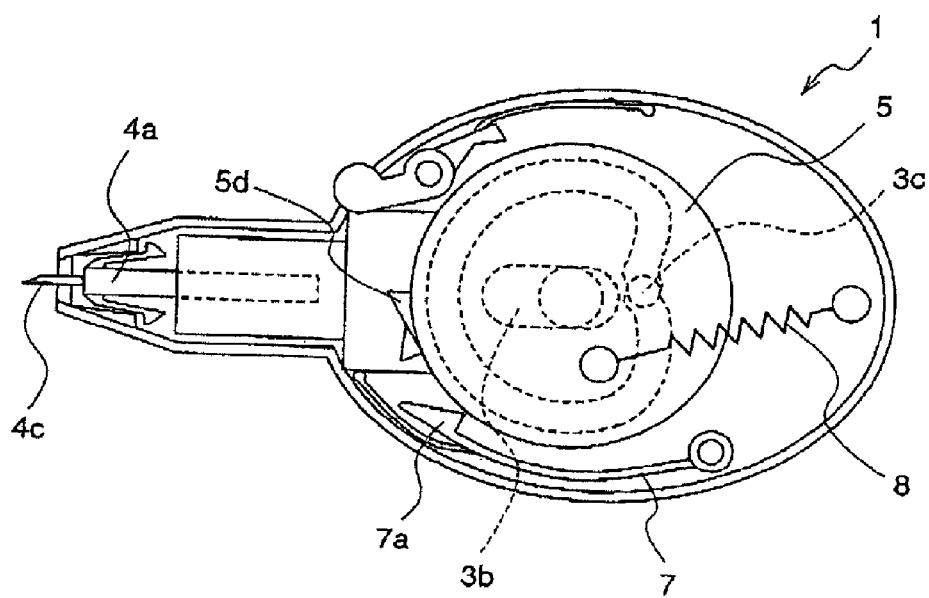
FIG. 4(c) is a plane view illustrating the puncture operation of the lancet according to the first embodiment, illustrating a puncture position where the puncture needle protrudes at maximum.

FIGS. 4(a)-4(c) are plane views for explaining the puncture operation of the lancet according to the first embodiment of the invention. To be specific, FIG. 4(a) shows the puncture needle set position where the ring spring is compressed at maximum, FIG. 4(b) shows the puncture-ready position, and FIG. 4(c) shows the puncture position where the puncture needle protrudes at maximum.

The operation will be described with reference to FIGS. 4(a)-4(c).

Initially, the puncture needle unit 4 in the state where the puncture needle body and the puncture needle cap shown in FIG. 3(a) or 3(b) are united is inserted into the lancet body 1 as shown in FIG. 3(c), and the puncture needle unit 4 is snugly fitted to the puncture needle fixing hole 3a of the slider 3, thereby setting the lancet 1 at the position shown in FIG. 4(a). With reference to FIG. 4(a), at the position where the shape of the slider 3 fits the shape of the puncture needle body 4a, the puncture needle unit 4 is inserted deeply, and the puncture needle cap 4e is rotated clockwise to sink the protrusion 4b into the catch claw 3d. Although the puncture needle body 4a is lightly press-inserted into the cap 4e, the puncture needle unit 4 can be reliably rotated by the rotation stop rib 4d or the safety claw 4f, and the slot 4g.

Thereafter, when the puncture needle cap 4e is pulled out, the puncture needle body 4a remains on the slider 3 side, and the needle 4c is exposed. However, the needle 4c is housed in the bottom case 2 of the lancet body 1. If the engagement of the protrusion 4b and the catch claw 3d is not tight, when the puncture needle cap 4e is pulled out, the puncture needle body 4a is pulled out together with the cap 4e, and the puncture needle body 4a is not set on the slider 3.

Further, in the case of the puncture needle unit shown in FIG. 3(b), when the puncture needle cap 4e is pulled out after performing the same operation as mentioned above, the elastic safety claw opens toward the outer circumference. Therefore, even when the engagement of the protrusion 4b and the catch claw 3d is released, the puncture needle body 4a interferes with the puncture needle stopper 2f and thereby it is not pulled out, resulting in more safety.

After the puncture needle body 4a is set in the position shown in FIG. 4(a), the cam ring 5 is rotated counterclockwise up to the puncture-ready position wherein the puncture needle is backed off into the lancet, and a force applied to the cam ring 5 by the ring spring 8 to rotate the cam ring 5 acts, as shown in FIG. 4(b), using a set ring described later or the like.

Next, the operation for rotating the cam ring 5 up to the puncture-ready position will be described with reference to FIGS. 5(a) and 5(b).

Figure 5A:
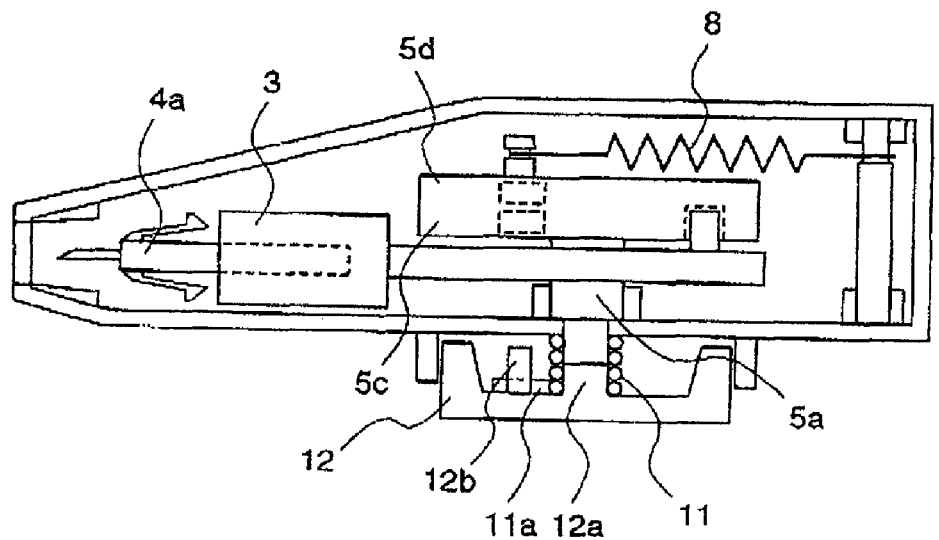
FIG. 5(a) is a side view of the lancet according to the first embodiment.
Figure 5B:
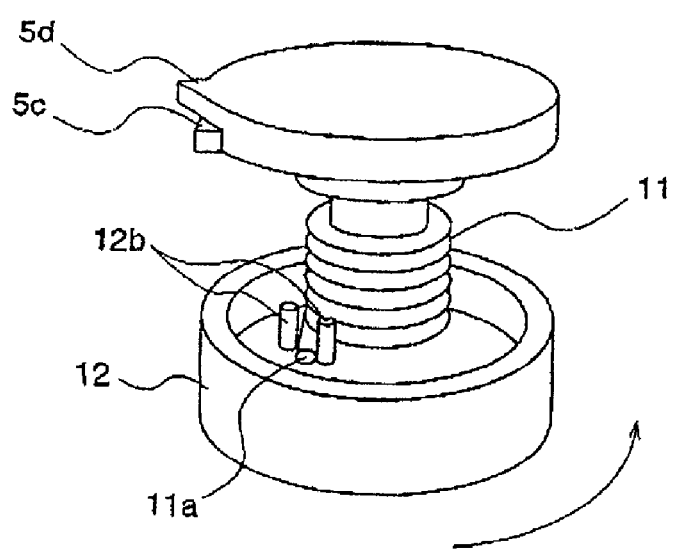
FIG. 5(b) is a side view of the lancet according to the first embodiment, illustrating a part of the lancet in detail.

FIG. 5(a) is a side view of the lancet according to the first embodiment, and FIG. 5(b) shows a portion of the lancet in detail.

In FIGS. 5(a) and 5(b), a set ring 12 is concentric with the cam ring support shaft 5a, and a clutch spring 11 for transferring the rotation force of the set ring 12 is snugly engaged and incorporated in the set ring support shaft 12a and the cam ring support shaft 5a. An end leg 11a of the clutch spring 11 is inserted between two fixed bosses 12b provided on the set ring 12, and fixed. As shown in FIG. 5(b), when the set ring 12 is rotated in the right-hand thread direction (shown by an arrow in FIG. 5(b)), the clutch spring 11 is tightened, and the cam ring support shaft 5a is rotated together, whereby the cam ring 5 is rotated counterclockwise in FIG. 4(a). On the other hand, when the set ring 12 is rotated in the left-handed thread direction (opposite direction to the arrow in FIG. 5(b)), the clutch spring 11 is loosened, and the cam ring support shaft 5a turns free, and thereby the cam ring 5 is not rotated. That is, the cam ring 5 can be rotated through the clutch spring 11, by rotating the set ring 12 counterclockwise.

By adding these elements, operability and reliability of the lancet body can be further improved.

After the puncture needle body 4a is set to the slider 3 in the position shown in FIG. 4(a), the set ring 12 is rotated counterclockwise until the cam ring claw 5c of the cam ring 5 contacts the stopper claw 6a of the stopper arm 6, resulting in a puncture possible state. At this time, if the set ring 12 is rotated clockwise, the clutch spring 11 is loosened, and the cam ring 5 turns free. While in this first embodiment the power of the set ring 12 is transferred to the cam ring 5 using the clutch spring 11, the present invention is not restricted thereto. Any mechanism may be employed so long as it can transfer the power of the set ring 12 in one direction. Further, the set ring is not restricted to that described above. Any mechanism may be employed so long as it can rotate the cam ring 5 from the outside of the lancet 1.

Through the above-mentioned operation, the lancet 1 is set in the puncture operation ready state shown in FIG. 4(b). Then, the stopper arm button 6b of the stopper arm 6 is pressed at the puncture operable position, whereby the stopper art is rotated counterclockwise, and the engagement of the stopper claw 6a and the cam ring claw 5c is released. Since the cam ring 5 is given a force counterclockwise by the ring spring 8, the cam follower 3c is positioned on the inclined part exceeding the inflection point at which the radius of the cam groove 5b changes. Therefore, the cam ring 5 starts to rotate counterclockwise. The cam follower 3c is guided by the cam groove 5b, the slider 3 slides in the puncture direction, and the needle 4c attached to the puncture needle body 4a also slides in the puncture direction.

FIG. 4(c) shows the puncture position wherein the needle 4c of the puncture needle body 4a protrudes at maximum from the lancet body 1, and puncture of a fingertip or the like is possible. From this position, the cam ring 5 is further rotated counterclockwise by both of the rotation force of the cam ring 5 and the counterclockwise force applied to the cam ring 5 by the ring spring 8, and stops at the puncture needle set position shown in FIG. 4(a) wherein the ring spring 8 is compressed at maximum. This position is a flat position exceeding the inflection point at which an area where the radius of the cam groove 5b changes is changed to an area where the radius of the cam groove 5b does not change. In this position, the slider is guided in the direction opposed to the puncture direction by the cam follower 3c guided by the cam groove 5b, and the puncture needle body 4a is recessed at maximum.

In the position shown in FIG. 4(a), the ring spring 8 does not generate a force for rotating the cam ring 5, and the cam ring 5 is most stable. If the cam ring rotates counterclockwise from the position of FIG. 4(a), the ring spring 8 generates a force for rotating the cam ring 5 clockwise, whereby the cam ring 5 returns to the position of FIG. 4(a).

Usually, in this position, the puncture needle body 4a is attached or detached to/from the puncture needle fixing hole of the slider 3. At this time, the cam follower 3c of the slider 3 is guided into the cam groove 5b, whereby the slider 3 is firmly held so as not to move.

Further, in a position between FIG. 4(c) and FIG. 4(a), the anti-return claw 5d formed on the cam ring 5 passes so that the ratchet claw 7a formed on the ratchet 7 is bent by the anti-return claw 5d. Therefore, even when the cam ring 5 starts to rotate clockwise, the anti-return claw 5d is engaged with the ratchet claw 7a to prevent the cam ring 5 from rotating clockwise. Accordingly, plural times of puncture onto a fingertip or the like by the needle 4c never occur.

When the puncture has been completed, in the position shown in FIG. 4(a), the puncture needle cap 4e is inserted deeply into the lancet body 1, and the slot 4g or the disposal slot 4h is engaged with the rotation stop rib 4d or the safety claw 4f of the puncture needle body. When the puncture needle cap 4e is rotated counterclockwise, the protrusion 4b is released from the catch claw 3d. Thereafter, the puncture needle cap 4e is pulled out, the puncture needle body 4a, which is press-inserted into the cap 4e, is pulled out together with the cap 4e. Of course, the needle 4c is protected by the cap 4e.

As described above, the lancet according to the first embodiment comprises the slider 3 which has the puncture needle holding mechanism at its one end; the cam ring 5 which has the continuous cam groove 5b, is rotatable about the support shaft, and has the claw for restricting the rotation; the ring spring 8 which applies a force to rotate the cam ring 5; the stopper arm 6 which is rotatable and is able to hold and release the rotation of the cam ring 5; and the ratchet 7 which is rotatable and restricts the direction of rotation of the cam ring 5. Further, the puncture needle unit comprises the puncture needle body 4a which is integrally molded with the protrusion 4b to be fitted to the lancet body, the rotation stop rib 4d or the elastic safety claw 4f, and the puncture needle 4c; and the puncture needle cap 4e into which the puncture needle body 4a is lightly press-inserted. Therefore, the puncture needle never hits the lancet body during the puncture operation, and the needle itself of the puncture needle unit protrudes only one time from the lancet body. Further, during attachment or detachment of the puncture needle, the slider is reliably held, whereby shock, sound, and vibration during puncture are reduced, and plural times of puncture by the puncture needle are avoided. As a result, it is possible to provide a lancet for blood collection and a puncture needle unit, which are easily handled and give less pain and fear to a patient.

Further, the lancet is provided with the set ring 12 which is rotatable about the same axis as the cam ring 5, and the clutch spring 11 for transferring the rotation force of the set ring 12 only in one direction, and the rotation force of the set spring 12 is transferred to the cam ring 5 through the clutch spring 11. Therefore, operability and reliability of the lancet body can be further improved.

While in the lancet 1 of the first embodiment the ratchet 7 is employed as an anti-reverse-rotation mechanism for preventing reverse rotation of the cam ring 5 after the puncture operation, the present invention is not restricted thereto. Any means may be employed so long as it has a mechanism for preventing reverse rotation of the cam ring 5.

Furthermore, while in the lancet 1 of the first embodiment the cam ring 5 is rotated using the ring spring 8, the present invention is not restricted thereto. Any means may be employed so long as it can apply a force to the cam ring 5 to rotate the cam ring 5 in a predetermined direction.

[Embodiment 2]

Figure 6:
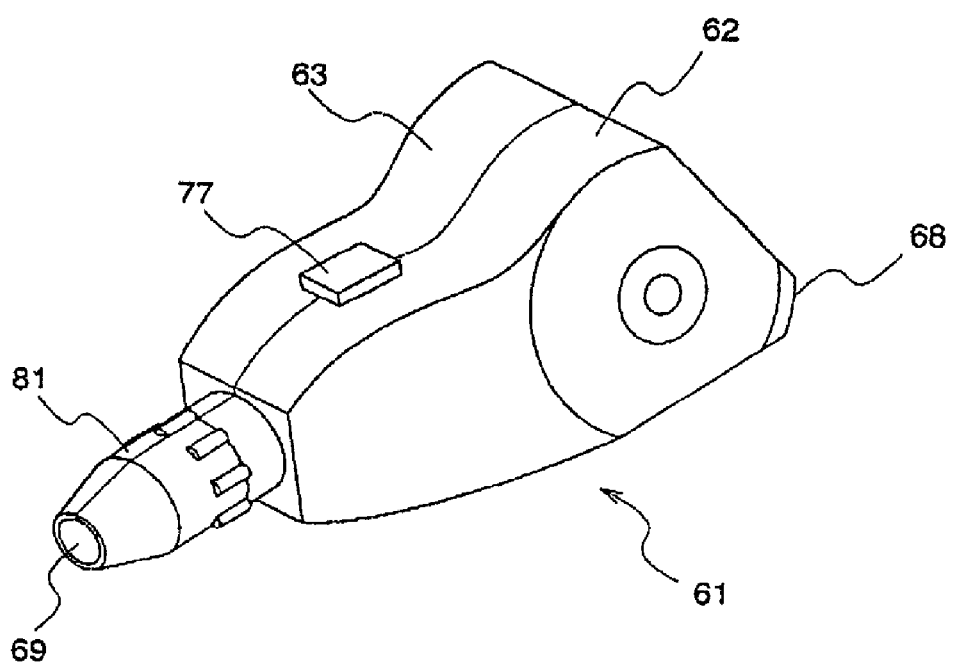
FIG. 6 is an external perspective view of a lancet according to a second embodiment of the present invention.
Figure 7A:
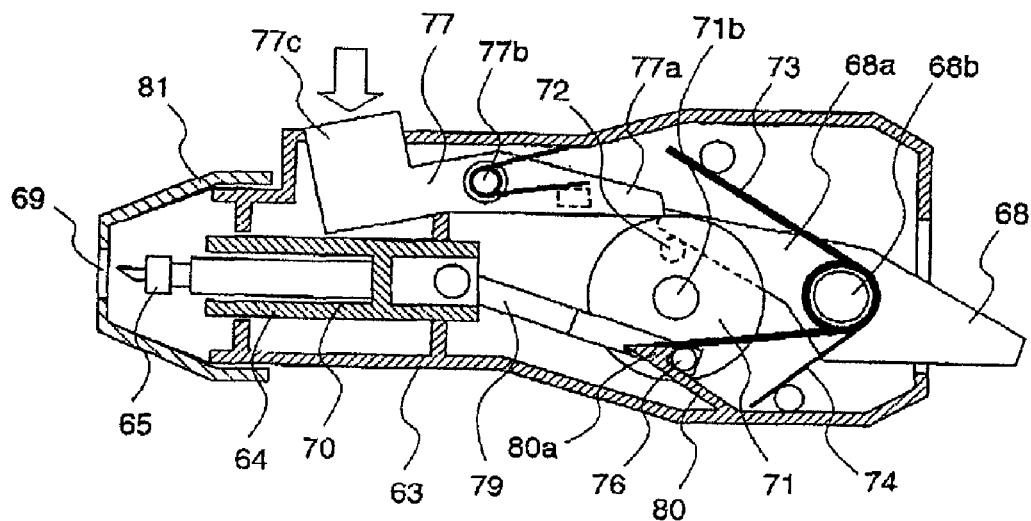
FIG. 7(a) is a cross-sectional view of the internal structure of the lancet according to the second embodiment.
Figure 7B:
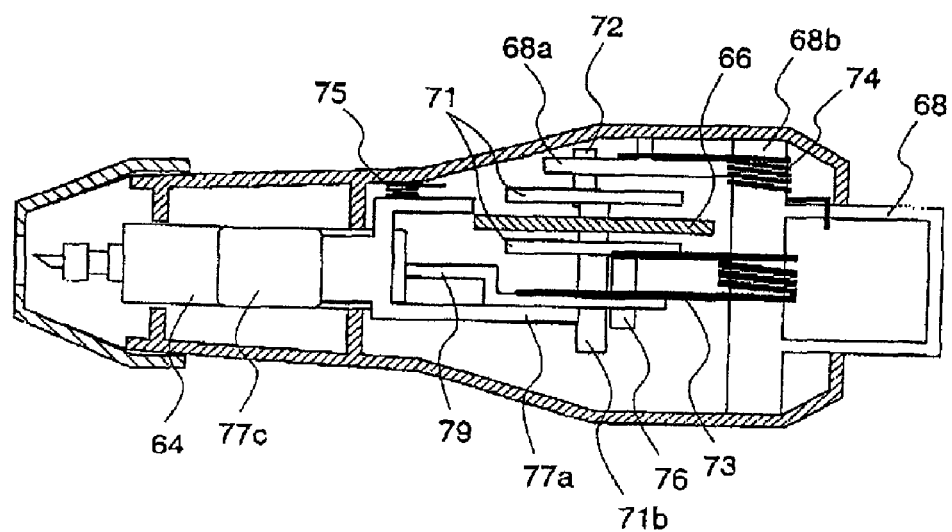
FIG. 7(b) is a top view of the internal structure of the lancet according to the second embodiment.
Figure 8:
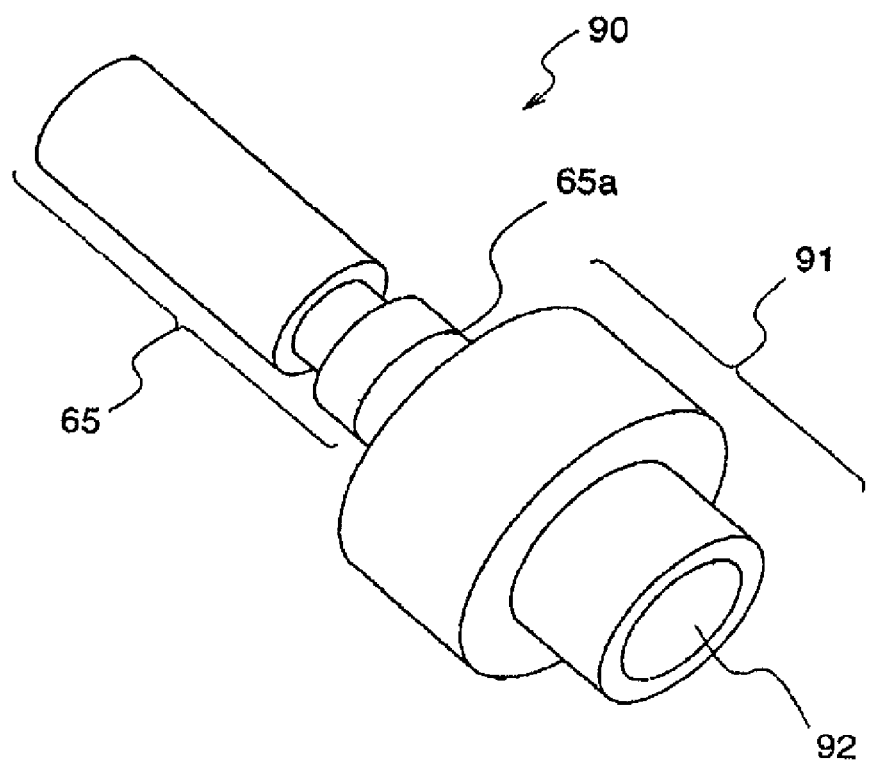
FIG. 8 is a perspective view illustrating a puncture needle unit to be used for the lancet according to the second embodiment.
Figure 9A:
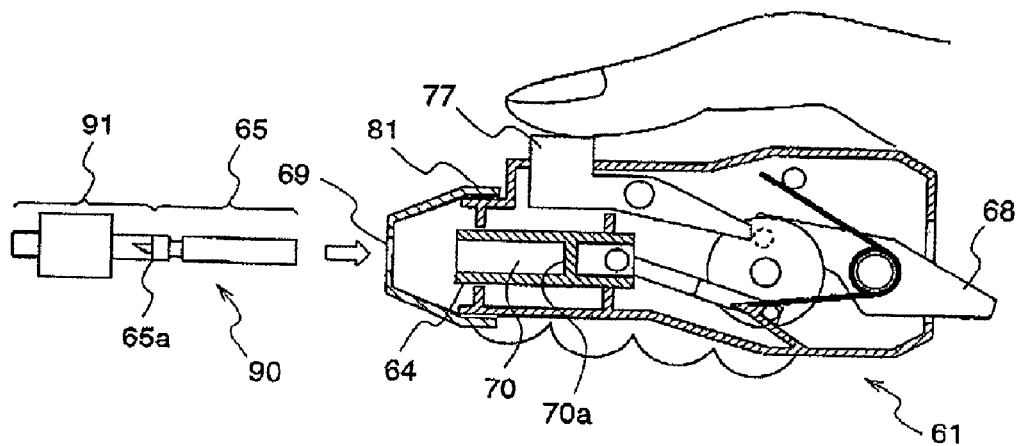
FIG. 9(a) is a diagram illustrating a method for loading a puncture needle on the lancet according to the second embodiment.
Figure 9B:
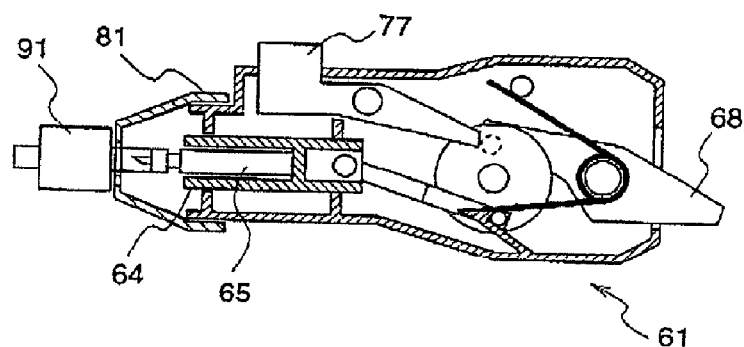
FIG. 9(b) is a diagram illustrating the method for loading the puncture needle on the lancet according to the second embodiment.
Figure 9C:
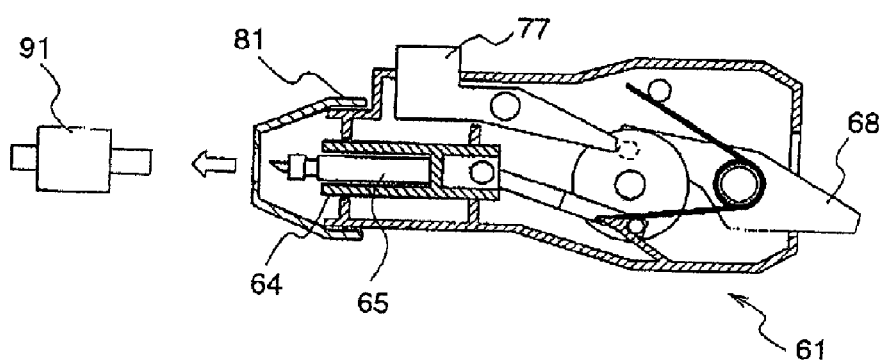
FIG. 9(c) is a diagram illustrating the method for loading the puncture needle on the lancet according to the second embodiment.

FIG. 6 is an external perspective view of a lancet according to a second embodiment of the present invention, FIG. 7 is a cross-sectional view illustrating the internal structure of the lancet, and FIG. 8 is an external perspective view of a puncture needle to be used for the lancet. As in the first embodiment, the lancet and the puncture needle are used to collect a small amount of blood for such as measurement of blood sugar. FIGS. 9(a)-9(c) are diagrams illustrating the procedures for setting the puncture needle into the lancet to perform puncture operation.

As shown in FIG. 6, a lancet 61 according to the second embodiment is provided with a puncture depth adjustment ring 81 having a puncture needle loading slot 69 at an end, a body top case 62, and a body bottom case 63.

In the body top case 62 and the body bottom case 63, as shown in FIGS. 7(a) and 7(b), there are provided a slider 64, a link mechanism 79, a flywheel 71, a puncture set lever 68, a stopper arm 77, a flywheel set spring 73, and the like. In the slider 64, a puncture needle 65 is inserted up to a predetermined depth.

The slider 64 is able to hold the puncture needle 65 in a puncture needle fixing hole 70 which is provided at an end of the slider 64, and is reversibly slidable in a linear direction.

The link mechanism 79 is coupled to the other end of the slider 64 on which the puncture needle is fixed at an end, and further, it is coupled to the flywheel 71 described later.

The flywheel 71 is coupled to the link mechanism 79 such that a wheel engagement pin 76 which is a rotation knot shaft to be a shaft of the other end of the link mechanism 79 coupled to the slider 64 is implanted in the flywheel 71.

The flywheel set spring 73 is implemented by a kick spring, and applies a force to the flywheel 71 to rotate the flywheel 71 in a predetermined direction so as to slide the slider 64 in the puncture direction through the link mechanism 79. While in this second embodiment a kick spring is used as the flywheel set spring 73, the present invention is not restricted thereto. Any means may be employed so long as it can apply a rotation force in a predetermined direction to the flywheel 71. For example, a ring spring shown in FIG. 1 may be employed.

The stopper arm 77 is able to stop the rotation of the flywheel 71 to which a force is applied by the flywheel set spring 73, or release the stopping. The stopper arm 77 is rotatable about a stopper arm support shaft 77b that is integrally molded with the bottom case 63. The stopper arm 77 has, at an end, a stopper claw 77a which is engaged with the wheel engagement pin 76 implanted in the flywheel 71 to fix the rotation of the flywheel, and has a stopper arm button 77c at the other end. The stopper arm spring 75 is integrally constituted with the stopper arm 77, and lightly applies a force to the stopper arm 77 clockwise. While in this second embodiment a kick spring as shown in FIG. 7(b) is used as the stopper arm spring 75, the present invention is not restricted thereto. Any spring may be employed so long as it can restrict the rotation of the stopper arm 77. For example, a plastic spring or a metal spring as shown in FIGS. 1 and 2 according to the first embodiment may be employed.

The puncture needle set lever 68 is engaged with the wheel set pin 72 on the flywheel 71, and rotates the flywheel 71 only in one direction, thereto set the flywheel 71 in a puncture-ready position.

Further, a puncture needle unit 90 according to the second embodiment is constituted as shown in FIG. 8. The puncture needle unit 90 is divided into a puncture needle body 65 and a puncture needle cap 91 with a puncture needle separation groove 65a as a boundary, and the body 65 and the cap 91 are connected to each other by a thin plastic film having a thickness of 0.1 mm or less in the puncture needle separation groove 65a. The puncture needle body 65 is set in a state where it is embedded in the puncture needle cap 91, and a disposal slot 92 for pulling out the puncture needle 65 after puncture has been carried out is provided at an end of the puncture needle cap 91. The shape of the puncture needle cap of the puncture needle unit 90 is not restricted to that shown in FIG. 8. For example, the puncture needle cap may have slots at the both ends thereof so that the puncture needle after the puncture operation can be inserted from the both ends, whereby setting and discarding of the puncture needle can be safely carried out from either slot. At this time, the puncture needle can be easily discarded by making the slot at the discarding side have a larger aperture.

Next, a description will be given of the operational procedures for setting the puncture needle 65 into the lancet 61 to prepare the lancet 61 for puncture.

Initially, in a state where the puncture needle set lever 68 is not set, the puncture needle loading slot 69 of the lancet 61 is fitted to the axis of the puncture needle 65, and the puncture needle unit 90 is pushed into the puncture needle loading slot 69 of the lancet 61 (FIG. 9(a)). At this time, the puncture needle unit 90 is pushed to a position where the rear end portion of the puncture needle 65 that is guided into the slider 64 of the lancet 61 presses the bottom surface 70a of the puncture needle fixing hole 70 of the slider 64. In this state, the puncture needle 65 is pressed into and snugly fitted to the inner wall of the puncture needle fixing hole 70 of the slider 64 (FIG. 9(b)). When the lancet 61 is pulled while twisting the puncture needle unit 90, since the puncture needle 65 is snugly fitted to the puncture needle fixing hole 70, the puncture needle 65 can be separated from the puncture needle cap 91. At this time, a force that pulls off the thin plastic film is generated in the puncture needle separation groove 65a that is positioned in the vicinity of the front end of the puncture needle 65. When the operator further applies a force against the pulling force, the puncture needle 65 can be separated from the puncture needle cap 91 (FIG. 9(c)).

Figure 10A:
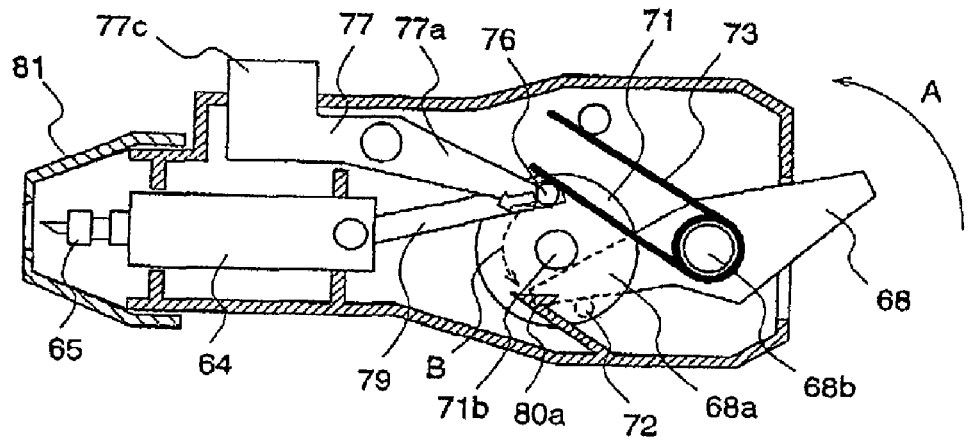
FIG. 10(a) is a diagram illustrating a method for preparing the lancet for puncture according to the second embodiment.
Figure 10B:
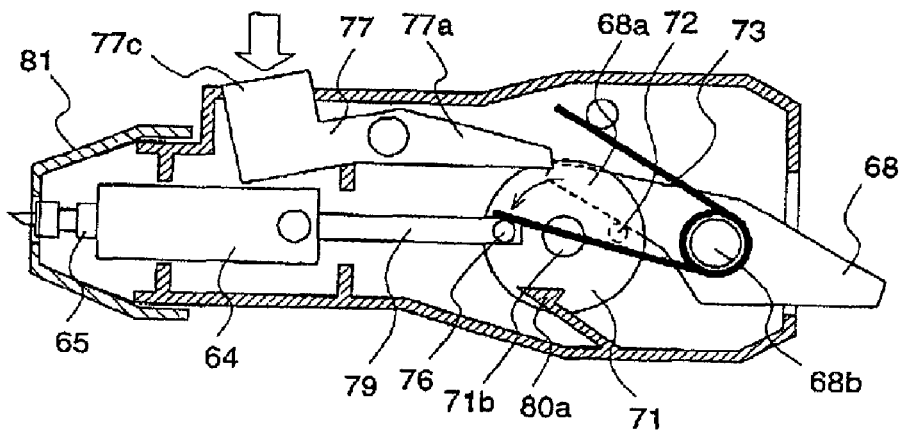
FIG. 10(b) is a diagram illustrating the method for preparing the lancet for puncture according to the second embodiment.
Figure 10C:
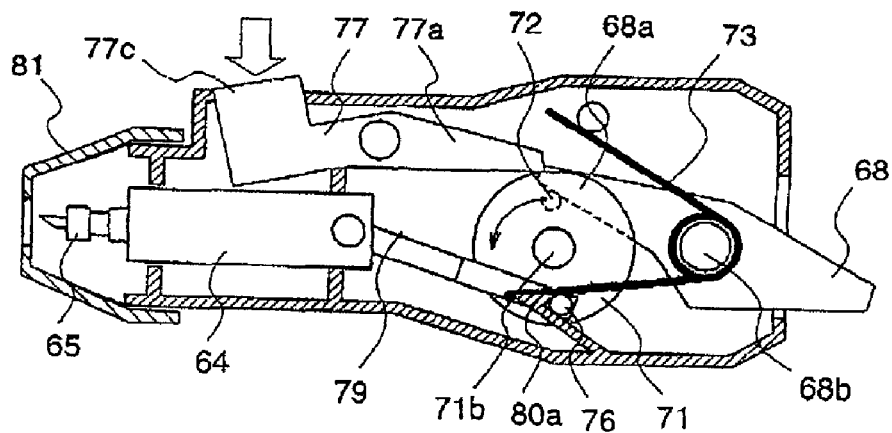
FIG. 10(c) is a diagram illustrating the method for preparing the lancet for puncture according to the second embodiment.

Thereafter, the puncture needle set lever 68 is tilted at a predetermined angle in the direction of arrow A to carry out puncture, whereby preparation for puncture is made (FIG. 10(a)). Hereinafter, a description will be given of the preparation operation and the puncture operation with reference to FIGS. 10(a)-10(c).

Initially, the puncture depth adjustment ring 81 provided at the front end of the lancet 61 is rotated about its axis to shift the position of the puncture depth adjustment ring 81 in the axis direction of the lancet 61, whereby a predetermined puncture depth of the puncture needle 65 is set.

Then, as shown in FIG. 9, the puncture needle 65 is loaded in the slider 64, and thereafter, the puncture needle set lever 68 is tilted at a predetermined angle in the direction of arrow A as shown in FIG. 10(a), whereby the wheel rotation lever 68a that is located in the opposite position from the puncture needle set lever 68 simultaneously rotates counterclockwise with respect to the rotation center 68b of the puncture needle set lever 68. Since the wheel rotation lever 68a rotates counterclockwise, the rotation lever 68a contacts the set pin 72 on the flywheel 71, and rotates the set pin 72, whereby the flywheel 71 rotates by a predetermined angle.

In the state where the puncture needle set lever 68 is tilted at a predetermined angle in the direction of arrow A, by setting the distance between the rotation center 68b of the puncture needle set lever 68 and the center axis of the set pin 72 longer than the distance between the rotation center 68b of the puncture needle set lever 68 and the rotation center 71b of the flywheel 71, the wheel rotation member (rotation lever) 68a on the puncture needle set lever 68 can rotate the flywheel 71 in the setting direction (direction of arrow B in FIG. 10(a)).

Further, as shown in FIG. 10(a), in the position where the flywheel 71 is rotated by the predetermined angle, the wheel engagement pin 76 provided on the flywheel 71 is maintained in the state where it is continuously pressed by the flywheel set spring 73, and therefore, the flywheel 71 tries to keep on rotating in the direction of arrow B in FIG. 10(a) (counterclockwise), and the flywheel 71 starts to rotate spontaneously by only the pressing force from the flywheel set spring 73, in a predetermined rotation position, i.e., in a rotation position after the distance between the center of the wheel engagement pin 76 and the rotation center 68b of the puncture needle set lever 68 becomes longer than the rotation shaft 71b of the flywheel 71 and the rotation center 68b of the puncture needle set lever 68. When the end of the wheel engagement pin 76 of the rotating flywheel 71 contacts the end of the stopper claw 77a positioned at the end of the stopper arm 77, the rotation of the flywheel 71 is stopped.

As described above, with the rotation of the flywheel 71, the slider 64 that is coupled to the flywheel 71 via the link 79 is slid in the axis direction of the lancet 61 by the link 79 that converts the rotation of the flywheel 71 into sliding of the slider 64. The wheel engagement pin 76 on the flywheel 71 and the slider 64 are engaged by the single link 79, and the flywheel 71 is rotated only in the predetermined direction (counterclockwise) as described above by the puncture needle set lever 68. Therefore, the wheel engagement pin 76 initially rotates in the direction of going away from the front end of the lancet 61, and the slider 64 sinks into the body of the lancet 61. Thereafter, as described above, the end of the wheel engagement pin 76 of the flywheel 71 is engaged with the stopper claw 77a which is provided at the end of the rotatably supported stopper arm 77, whereby the rotation of the flywheel 71 is stopped, and simultaneously, the motion of the slider 64 is stopped. At this time, the axis center of the wheel engagement pin 76 is positioned on the slider side with respect to the rotation center of the flywheel 71, and the flywheel 71 conserves the rotation power by the force of the flywheel set spring 73, and thus setting is completed (FIG. 10(a)). In this way, the wheel engagement pin 76 is constituted as an engagement mechanism for preparation for puncture operation, which fixes the slider to a start position of one reciprocating operation of the slider in its axis direction.

Thereafter, when the stopper arm button 77c is pressed, the stopper arm 77 rotates about the shaft 77b, and the engagement of the stopper claw 77a and the wheel engagement pin 76 is released, whereby the flywheel 71 rotates at a stroke in the direction of arrow B (counterclockwise) about the shaft 71b. At this time, the slider 64 that is coupled to the flywheel 71 by the link 79 starts sliding (linear motion) from the inside of the lancet 61 toward the outside. Thereafter, with the rotation of the flywheel 71, the slider 64 protrudes at maximum from the lancet 61 (FIG. 10(b)), and then it returns into the lancet 61 by the pressing force of the flywheel set spring 73 and the inertial force of the flywheel 71. Further, at this time, the puncture needle set lever 68 returns to the initial position by the rotation force of the engaged set pin 72 and the force applied by the lever return spring 74. Even when the puncture needle set lever 68 is not provided with the lever return spring 74, the puncture needle set lever 68 can be returned to the initial position by the rotation force of the set pin 72. However, provision of the lever return spring 74 reduces the load on the rotation of the flywheel 71 during the puncture operation.

During the return operation, the wheel engagement pin 76 at the end of the link 79 reaches a position that is most distant from a line connecting the rotation center 68b of the puncture needle set lever 68 and the rotation center 71b of the flywheel 71, and the wheel engagement pin 76 attenuates while reciprocating with the position in the center by the recovery force of the flywheel set spring 73 until it stops in the position, and finally, it stops. At this time, it is necessary to prevent the slider 64 from returning back to the direction in which the slider 64 protrudes from the lancet 61. For this purpose, the body bottom case 63 is provided with an anti-reverse-rotation mechanism 80 that is engaged with the wheel engagement pin 76 so as not to return the operation of the wheel engagement pin 76 back into the puncture position direction, thereby to prevent reverse rotation of the flywheel after the puncture operation. Moreover, in order to prevent an anti-reverse-rotation claw provided at an end of the anti-reverse-rotation mechanism 80 from becoming a load onto the rotation of the flywheel 71, an angle of attack is provided at then end of the anti-reverse-rotation claw 80a (FIG. 10(c)).

When the flywheel 71 rotates to a predetermined position, the wheel engagement pin 76 contacts the anti-reverse-rotation claw 80a at the end of the flexible anti-reverse-rotation mechanism 80. When the flywheel 71 continues to rotate, the wheel engagement pin 76 gets on the upper surface of the anti-reverse-rotation claw 80a, and slides while bending and pushing down the anti-reverse-rotation mechanism 80 to the lower left in the figure. At the instant when the wheel engagement pin 76 passes over the upper surface, the anti-reverse-rotation claw 80a returns to the initial state, and catches the wheel engagement pin 76. That is, since the anti-reverse-rotation claw 80a is provided with the above-mentioned angle of attack, the wheel engagement pin 76 can smoothly get on the upper surface of the anti-reverse-rotation claw 80a at a preferable angle and pass the claw 80a so that it does not become load on the rotation of the flywheel 71. Thus, the lancet can prevent reverse rotation of the flywheel 71 without applying load on the rotation of the wheel engagement pin 76 (FIG. 10(c)).

Next, a description will be given of the operation of discarding the puncture needle 65 after the puncture operation has been completed.

Figure 11A:
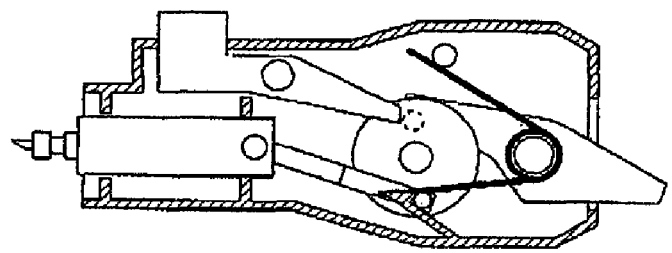
FIG. 11(a) is a diagram illustrating a method for discarding a puncture needle attached to the lancet according to the second embodiment.
Figure 11B:
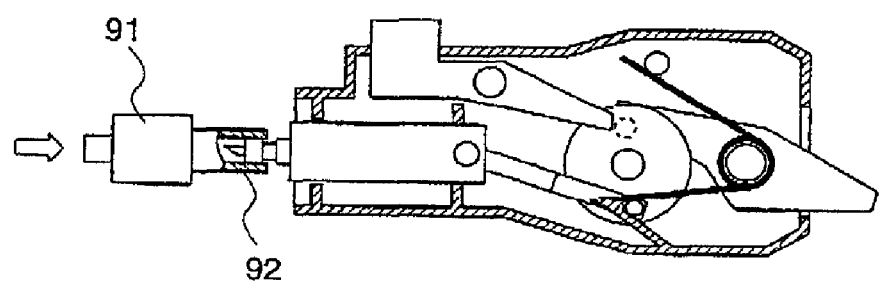
FIG. 11(b) is a diagram illustrating the method for discarding the puncture needle attached to the lancet according to the second embodiment.
Figure 11C:
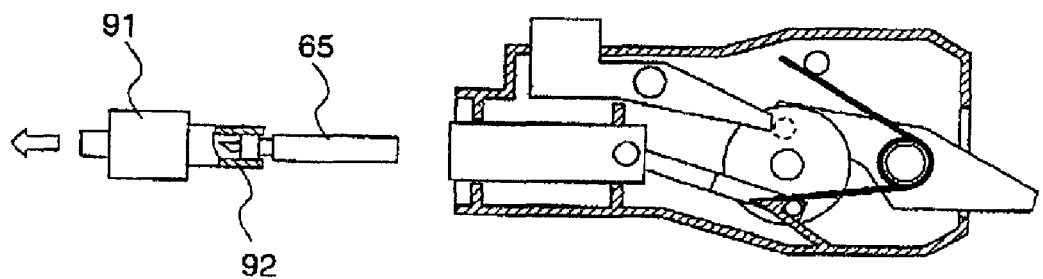
FIG. 11(c) is a diagram illustrating a method for discarding the puncture needle attached to the lancet according to the second embodiment.

In the state where the above-mentioned puncture operation has been completed, the puncture depth adjustment ring 81 on the puncture needle loading slot 69 side of the lancet 61 is removed, the front end of the puncture needle 65 is exposed (FIG. 11(a)). In this state, the shaft of the disposal slot 92, which is provided at an end of the puncture needle cap 91 the other end of which has covered the front end of the puncture needle 65 before used, is fitted to the front end of the puncture needle 65, and the front end of the puncture needle 65 is pressed into the disposal slot 92 to snugly insert the needle 65 into the slot 92, whereby the puncture needle 65 is captured into the disposal slot 92 (FIG. 11(b)). Thereafter, the puncture needle cap 91 having the puncture needle 65 is pulled out of the lancet 61, whereby discarding of the used puncture needle 65 is completed (FIG. 11(c)), and the puncture needle 65 can be discarded safely and easily without exposing the front end of the puncture needle.

Figure 12:
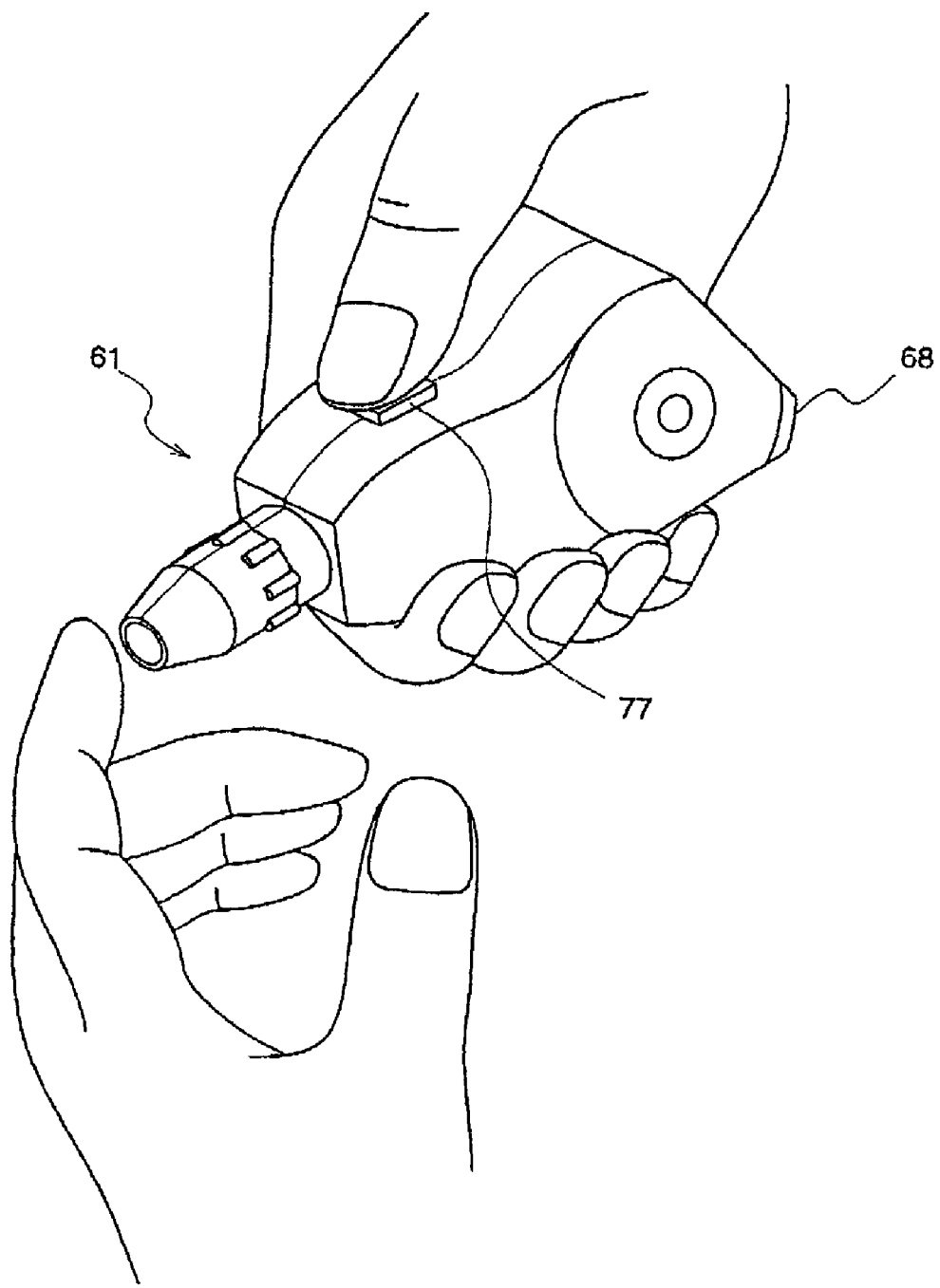
FIG. 12 is a perspective view illustrating a puncture operation by the lancet according to the second embodiment.
Figure 13:
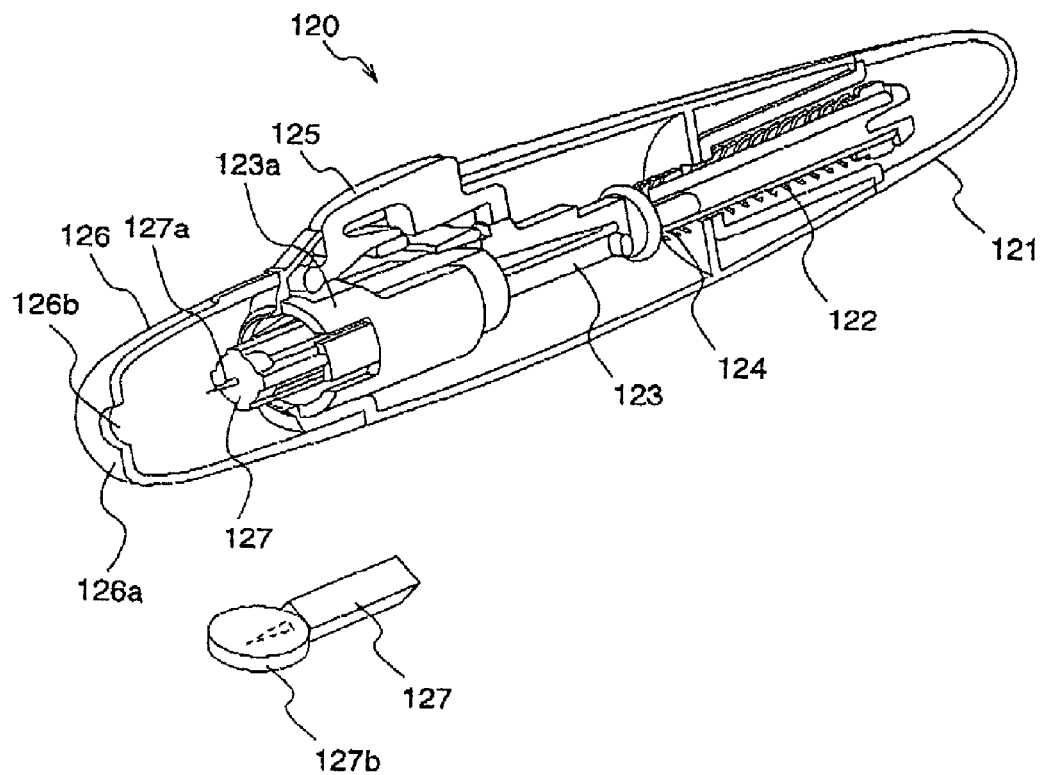
FIG. 13 is a perspective view illustrating the conventional lancet.

Accordingly, it is possible for an operator to easily perform puncture during measurement of blood sugar or the like, by repeating a series of operations as described above. That is, the operator can complete setting of a puncture needle by rotating the puncture needle set lever 68, and perform puncture and blood collection as shown in FIG. 12 by pressing the stopper arm 77 in the puncture-ready state.

As described above, the lancet for blood collection according to the second embodiment is provided with the slider 64 that is able to hold the puncture needle 65 at an end thereof, and is reversibly slidable in a linear direction; the flywheel 71 that is rotated while being supported by the wheel rotation shaft 71b; the link 79 having an end engaged with the other end of the slider 64, and the other end engaged with the wheel engagement pin 76 that is implanted in the flywheel 71 as its rotation knot shaft, thereby to convert the rotation of the flywheel 71 into sliding of the slider 64; the flywheel set spring 73 for applying a force to the flywheel 71 to rotate the flywheel 71 in a constant direction; the set lever 68 for setting the flywheel 71 in a puncture-ready state by rotating the flywheel 71 only in one direction with the set pin 72 implanted in the flywheel 71 being engaged with the set lever 68; the stopper art 77 that has an end contacting the wheel engagement pin 76, and is externally operable; and the anti-reverse-rotation mechanism 80 that is provided on the body case, and stops the wheel engagement pin 76. The flywheel set spring 73 applies a force to the wheel engagement pin 76 to rotate the flywheel 71 about its rotation axis only in one direction. Therefore, it is possible to reliably rotate the flywheel 71 to make the puncture needle protrude from the lancet body for puncture operation, and back off the puncture needle immediately after the puncture operation, with the simple construction. Further, the anti-reverse-rotation mechanism 80 prevents the puncture needle from protruding from the lancet body again due to vibration of the flywheel set spring 73 after the puncture needle is backed off into the lancet body. Thereby, vibration or impulsive sound of the lancet body during puncture can be avoided to reduce pain and unconformity of the patient during puncture.

While the lancet 61 according to the second embodiment is provided with the puncture depth adjustment ring 81 that is united with the puncture needle loading slot 69, the lancet 1 may dispense with the puncture depth adjustment ring 81 as shown in FIG. 1. In this case, the front end of the lancet is shaped so that setting and discarding of the puncture needle can be carried out, whereby it becomes unnecessary to disconnect the puncture depth adjustment ring 81 during discarding of the puncture needle, and the discarding operation can be safely carried out. Conversely, it is possible to provide a puncture depth adjustment ring 81 at the front end of the lancet 1 according to the first embodiment.

Further, while in the lancet according to the second embodiment, the anti-reverse-rotation mechanism 80 is integrally arranged with the body case, the present invention is not restricted thereto. Any mechanism may be employed so long as it can prevent reverse rotation of the flywheel 71, for example, the ratchet 7 shown in FIG. 1 may be employed.

Furthermore, as in the first embodiment, the puncture needle 65 may be provided with a protrusion 4b and a rotation stop rib 4d as shown in FIG. 3(*a*). In this case, the puncture needle cap 91 and the puncture needle fixing hole 70 are shaped so as to be fitted to the protrusion and the rotation stop rib. Further, the puncture needle fixing hole 70 may be provided with a catch claw 3d as shown in FIG. 3(*c*). Thereby, setting of the puncture needle is facilitated.

Furthermore, as in the first embodiment, the puncture needle 65 may be provided with a safety claw 4f as shown in FIG. 1. At this time, a puncture needle stopper 2f as shown in FIG. 1 may be provided in the puncture needle loading slot, whereby the puncture needle is prevented from dropping. Further, at this time, the puncture needle cap 91 is shaped so as to be fitted to the safety claw, whereby it can function as the above-mentioned rotation stop rib.

According to the present invention, it is possible to provide a lancet and a puncture needle unit, which reduce shock, sound, and vibration during puncture, prevent plural times of puncture by a puncture needle, reduce pain and fear of a patient, and are easy to handle and highly reliable. Therefore, the lancet and the puncture needle unit are useful for performing measurement that requires blood collection.

What is claimed is:

1. A lancet for puncturing a human body to collect bodily fluids from the human body, comprising:
    a puncture needle;
    a slider which is able to hold said puncture needle at one end, and is reversibly slidable in a linear direction so that a puncture operation by said puncture needle is carried out;
    a cam ring which is flat-shaped and rotatable about an axis thereof, has a cam groove that is engaged with a cam follower provided on the slider within a rotation plane of the cam ring, and slides the slider by the rotation of the cam ring;
    an elastic force application member for applying a rotation force in a predetermined direction to the cam ring to slide the slider in a puncture direction;
    a stopper arm for stopping the rotation of the cam ring to which a force is applied by the elastic force application member, or releasing the stopping; and
    an anti-reverse-rotation mechanism which is implemented by a ratchet mechanism for preventing reverse rotation of the cam ring after the puncture operation.

2. A lancet as defined in claim 1 wherein
    said anti-reverse-rotation mechanism releases the stopping of rotation of the cam ring to which a force is applied by the elastic force application member, by the releasing operation of the stopper arm; and
    when the slider moves with the rotation of the cam ring and thereby a puncture operation is carried out and then the slider moves in a direction that goes apart from the puncture direction with further rotation of the cam ring, the anti-reverse-rotation mechanism restricts the rotation of the cam ring in one direction so as to prevent the slider from moving in the puncture direction again.

3. A lancet as defined in claim 1 wherein
    said stopper arm has a stopper claw that contacts a cam ring claw of the cam ring, in a puncture-ready position where said puncture needle is backed off into the lancet, and a rotation force applied to the cam ring by the elastic force application member is active;
    when the stopper arm is pressed and rotated in the above-mentioned state, the contact of the stopper claw of the stopper arm and the cam ring claw is released, whereby the cam ring rotates in a predetermined position; and
    when the slider slides in the puncture direction by the rotation of the cam ring and thereby the cam ring rotates exceeding a maximum protrusion position of said puncture needle, an anti-reverse claw of the cam ring passes over a ratchet claw of the ratchet mechanism while bending the ratchet mechanism, and catches the ratchet claw to prevent the cam ring from rotating in the opposite direction.

4. A lancet as defined in claim 1 wherein
    said stopper arm has a stopper for restricting an amount of rotation of the stopper arm toward the cam ring; and
    said ratchet mechanism has a stopper for restricting an amount of rotation of the ratchet toward the cam ring.

5. A lancet as defined in claim 1 further comprising:
    a set ring which is rotatably provided on a same axis as the cam ring; and
    a force transfer mechanism for transferring a rotation force of the set ring only in one direction;
    wherein the rotation force of the set ring is transferred to the cam ring through the force transferring mechanism.

6. A lancet of claim 1 wherein said elastic force application member is implemented by a ring spring.

7. A lancet as defined in claim 1 wherein said puncture needle has a safety claw which is engaged with the inner surface of an external case of the lancet to prevent said puncture needle from dropping when said puncture needle is detached from the lancet.

8. A lancet as defined in claim 1 wherein
    said slider has a fitting and fixing hole for fixing said puncture needle; and
    said puncture needle is a puncture needle unit comprising a puncture needle body and a puncture needle cap, and the puncture needle body has
        a puncture needle main part having a needle at a front end thereof,
        a protrusion to be fitted and fixed to the fitting and fixing hole, at an external surface of a base portion of the puncture needle main part, and
        a rotation stop rib for the puncture needle cap that covers the puncture needle body, at a side surface of an upper portion of the puncture needle body, and
    the puncture needle cap is fitted to the rotation stop rib and is lightly pressed into the puncture needle body to cover the puncture needle body.

9. A lancet as defined in claim 8 wherein
    in said puncture needle unit, the puncture needle main part is snugly fitted and attached to the lancet with the puncture needle cap being attached to the puncture needle body part; and
    after the puncture needle main part is attached to the lancet, the puncture needle cap is removed from the puncture needle main part.

10. A lancet as defined in claim 8 wherein
in said puncture needle unit detaches the puncture needle main part from the lancet as follows:
the puncture needle cap is pressed in and snugly fitted to the puncture needle main part after performing the puncture operation; and
the puncture needle main part is removed together with the puncture needle cap from the lancet body together.

11. A lancet as defined in claim 8 wherein said puncture needle cap is cylindrical in shape, and has protection slots for protecting said puncture needle after performing the puncture operation from the lancet body, which slots are formed from both of an end and the other end of the cylindrical shape.

12. A lancet as defined in claim 8 wherein said puncture needle cap is cylindrical in shape, and has a protection slot for protecting said puncture needle, which is formed from an end of the cylindrical shape, and a disposal slot for taking said puncture needle after performing the puncture operation from the lancet body and discarding the needle, which is formed from the other end of the cylindrical shape, and fitting of said puncture needle to the disposal slot is easier than fitting of said puncture needle to the protection slot.

13. A lancet as defined in claim 12 wherein said disposal slot of the puncture needle cap has an opening that is larger than an opening of the protection slot.

14. A lancet as defined in claim 8 wherein
said puncture needle body has a safety claw which is engaged with the inner surface of an external case of the lancet to prevent said puncture needle from dropping when the puncture needle body is detached from the lancet; and
said puncture needle cap is lightly pressed into the puncture needle body while being fitted to the safety claw, to cover the puncture needle body.

\* \* \* \* \*